United States Patent [19]

Kubik et al.

[11] 4,172,122
[45] Oct. 23, 1979

[54] SUBSTANTIVE SUNSCREENING COMPOSITIONS

[75] Inventors: Donald A. Kubik, Somerset Township, St. Croix County, Wis.; James B. Stake, Woodbury, Minn.

[73] Assignee: Minnesota Mining and Manufacturing Company, Saint Paul, Minn.

[21] Appl. No.: 820,122

[22] Filed: Jul. 29, 1977

[51] Int. Cl.² ............ A61K 7/00; A61K 7/42; A61K 7/44
[52] U.S. Cl. .............. 424/59; 260/23 AR; 260/31.2 R; 260/33.6 UA; 424/60; 424/81
[58] Field of Search ............ 424/59, 81, 60

[56] References Cited

U.S. PATENT DOCUMENTS

| | | | |
|---|---|---|---|
| 3,058,886 | 10/1962 | Kreps | 424/59 |
| 3,123,647 | 3/1964 | Duennenberger | 424/59 X |
| 3,215,724 | 11/1965 | Strobel et al. | 424/59 X |
| 3,406,238 | 10/1968 | Freyermuth et al. | 424/59 X |
| 3,454,586 | 7/1969 | Suh et al. | 424/59 X |
| 3,574,822 | 4/1971 | Shepherd et al. | 424/59 X |
| 3,670,073 | 6/1972 | Shepherd et al. | 424/59 X |

FOREIGN PATENT DOCUMENTS

| | | | |
|---|---|---|---|
| 1958336 | 6/1973 | Fed. Rep. of Germany | 424/59 |
| 1305872 | 11/1961 | France | 424/59 |
| 819452 | 9/1959 | United Kingdom | 424/59 |

*Primary Examiner*—Allen J. Robinson
*Attorney, Agent, or Firm*—Cruzan Alexander; Donald M. Sell; Carolyn A. Bates

[57] ABSTRACT

Water resistant sunscreening compositions are disclosed comprising a cosmetically-acceptable oil base, at least one water-insoluble ultraviolet light absorbing material which is soluble in the oil base, and a water insoluble acrylate polymer having a solubility parameter of 6 to 10 in weak hydrogen bonding solvents. The acrylate polymer serves to bind the ultraviolet light absorber to the skin and render it resistant to removal by water.

17 Claims, No Drawings

SUBSTANTIVE SUNSCREENING COMPOSITIONS

This invention relates to cosmetic formulations which provide water-resistant protection against the erythema-causing radiation of sunlight. More particularly, the invention relates to sunscreening compositions wherein an ultraviolet light-absorbing material placed on the skin is rendered more water resistant by means of a polymeric binder.

Although the potentially damaging effects of sunlight on human skin have been well publicized, many people have occupations which require them to be exposed to the sun for long periods of time. Many others choose to spend their leisure time outdoors playing tennis or golf, swimming, fishing, skiing or sunbathing. To protect human skin against erythema-causing radiation from the sun, a variety of sunscreening compositions have been developed containing compounds which absorb ultraviolet light in the erythemal region of 290 to 320 nanometers. To prolong their effectiveness, these compositions should be resistant to removal from the skin by water or perspiration.

A variety of water-resistant or "substantive" sunscreening compositions are known in the art. Substantivity has been achieved by chemically modifying the ultraviolet light absorber to increase its interaction with skin (e.g. esterifying derivatives of salicyclic acid and p-aminobenzoic acid with lecithins, choline, or quaternized imidazoles as described in U.S. Pat. No. 3,506,758), by copolymerizing ultraviolet light absorbing monomers with other monomers to form water-resistant films, (see, for example U.S. Pat. Nos. 3,529,055 and 3,864,473) or by increasing the water insolubility of the ultraviolet light absorber.

Alternatively, polymeric films have been used to enhance substantivity of sunscreening compositions. U.S. Pat. No. 3,784,488 describes cosmetic formulations comprising a volatile organic solvent, a nonvolatile liquid organic compound such as an ultraviolet light absorber and a film-forming polymer. The compositions contain a high level of the nonvolatile organic compound in proportion to the film-forming polymer. The polymer must be insoluble in, and immiscible with, the organic compound and be more soluble in the solvent than the organic compound. The compositions form continuous films on the skin, and the organic compound is trapped within voids in the film. Acrylate polymers containing 5 to 30 weight percent of a carboxylic acid group are preferred.

The use of the acid form of crosslinked ethylene-maleic anhydride copolymers to retain ultraviolet light absorbers on skin is disclosed in U.S. Pat. No. 3,821,363. These polymers form a gel in water or water-alcohol mixtures. U.S. Pat. No. 3,895,104 describes sunscreening compositions wherein film forming polyamides enhance retention of the ultraviolet light absorber on the skin. Alcoholic mixtures are used as the vehicle in these compositions.

U.S. Pat. No. 3,590,118 describes the use of polymers of alpha-beta unsaturated carbonyl monomers to control the release of insect repellent compounds from skin and enhance water-resistance. A continuous polymeric film is cast on the skin out of an alkaline water or a hydroalchoholic solution.

Prior art compositions utilizing polymers or polymeric film formers suffer from a number of disadvantages. Since their object is to form a tough, continuous film on the skin, these compositions cannot tolerate large amounts of oil and other emollients which would overplasticize the films. As a result, the compositions are generally applied from alcoholic solutions, which can be irritating and drying to the skin, difficult to apply evenly, and which provide minimal moisturization. Furthermore, the resulting films tend to provide poor wet abrasion resistance.

The sunscreening composition of the present invention overcomes many of the problems associated with prior art compositions by providing compositions which are oil-based and thereby have a soothing and moisturizing effect on the skin. The compositions give the skin a moist, glossy appearance which many people find aesthetically pleasing and which also aids the user in applying the compositions evenly. The compositions are surprisingly resistant to removal by water and perspiration.

According to the present invention sunscreening compositions containing an oil base and oil-soluble ultraviolet light absorbing material to filter out the damaging rays of the sun are made more water-resistant by the addition of oil-soluble acrylate polymers which bind the ultraviolet light absorber to the skin. A major requirement of the compositions is that both the polymers and the ultraviolet light absorbers must be soluble in the oil base and insoluble in water.

The present invention provides dermally-nonirritating sunscreening compositions comprising a nonvolatile, cosmetically-acceptable oil base; an effective amount of at least one ultraviolet light absorbing material which is substantially water-insoluble and soluble in the oil base; and at least 0.5 percent by weight, based on the weight of the oil base, of a water-insoluble acrylate polymer having a solubility parameter between 6 and 10 in weak hydrogen bonding solvents.

While the acrylate polymers used in the compositions of the invention may be film-formers, the resulting oil film is not a continuous polymeric film. Rather, the oil film consists primarily of nonvolatile oils having dissolved therein small amounts of polymer binder. Many of the polymers used in the compositions of the invention can act as emulsifying agents as well as binding agents. Water may be added to compositions containing these polymers to form water-in-oil emulsions which leave water-resistant oil films on the skin.

The cosmetically-acceptable oil base of the compositions may be any oil or mixture of oils which are conventionally used in the cosmetic art. Examples of suitable oils include saturated fatty esters and diesters such as isopropyl palmitate, isopropyl myristate, butyl stearate, diisopropyl adipate, dioctyl sebacate, propylene glycol dipelargonate, etc., paraffin oils and waxes, animal and vegetable oils including mink oil, coconut oil and derivatives, palm oil, corn oil, soybean oil, cocoa butter, sesame oil, and the like, lanolin derivatives, fatty alcohols such as isostearyl alcohol, isocetyl alcohol, and straight chain alcohols from $C_6$–$C_{18}$, and certain petroleum distillates which are toxicologically safe such as $C_8$–$C_{18}$ isoparaffin hydrocarbon solvents. The oils mentioned in this list are merely examples and are not intended to limit the invention in any way. In general, any nonvolatile material or mixtures thereof which are toxicologically safe for human use and which have solubility parameters in the range of 6 to 10 may be used as the oil base of these compositions.

The term "ultraviolet light-absorbing material" as used herein refers to any compound or combination of compounds capable of absorbing ultraviolet light in the erythemal range of 290 to 320 nanometers and which are safe for use on human skin. In order to be useful in the compositions of the invention, the ultraviolet light-absorbing material must be water insoluble and soluble in the oil base. Examples of such ultraviolet light-absorbing compounds include, but are not limited to, p-aminobenzoates, p-dialkylaminobenzoates, salicylates, cinnamates, benzophenones, and acetophenones. Compounds which absorb ultraviolet radiation having wavelengths above 320 nanometers can be added to prevent sunburn potentiating effects or to help protect people who are photo-sensitized to long ultraviolet radiation. Compounds which absorb ultraviolet light below 290 nanometers may be incorporated into compositions to protect workers who are exposed to these wavelengths (e.g. welders).

The compositions generally contain between about 0.5 and 10.0 percent by weight of the ultraviolet light absorbing material, depending upon the degree of sunburn protection desired.

Acrylate polymers used as binders for the ultraviolet light absorbers include homopolymers, copolymers, terpolymers, etc., derived from the same or different ester monomers of the formula:

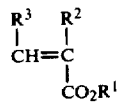

Formula I where $R^1$ is alkyl containing 1 to 18 carbon atoms in straight or branched-chain configuration, $R^2$ is hydrogen, methyl or $-CH_2CO_2H$, and $R^3$ is hydrogen, $-CO_2H$ or $CO_2R^1$, provided that when $R^3$ is $-CO_2H$ or $-CO_2R^1$, $R^2$ is hydrogen. The polymer may optionally contain up to 50 mole percent of the same or different acid monomers of the formula:

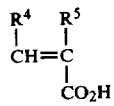

Formula II where $R^4$ is hydrogen or $-CO_2H$, and $R^5$ is hydrogen, methyl, or $-CH_2CO_2H$, provided that when $R^4$ is $-CO_2H$, $R^5$ is hydrogen.

The acrylate polymers can be prepared from the corresponding alkyl esters of acrylic, methacrylic, itaconic or maleic acid, wherein the ester alkyl groups may contain 1 to 18 carbon atoms and are exemplified by methyl, ethyl, butyl, methylisoamyl, n-hexyl, 2-ethylhexyl, isooctyl, isodecyl, lauryl, octadecyl, stearyl groups and the like. The most preferred esters are the acrylates and methacrylates with alkyl groups containing 6 to 18 carbon atoms. Esters wherein the alkyl group contains less than four carbon atoms may be included in small amounts, e.g. less than 10 mole percent. However, in order to achieve the requisite solubility parameter, the polymers should generally not contain a significant amount of lower alkyl ester monomers.

The acrylate polymers may optionally contain up to 50 mole percent of the unesterified α,β-olefinically unsaturated carboxylic acids of Formula II such as acrylic acid, methacrylic acid, maleic acid or itaconic acid. The presence of the carboxylic acid monomer enhances the removability of the compositions with soap and water. Polymers containing carboxylic acid groups are also useful as emulsifiers and should be used in the water-in-oil emulsion formulations.

The preferred polymers for the oil composition (as distinguished from the water-in-oil emulsions) are derived from 0 to 30 mole percent of the acid monomers and from 100 to 70 mole percent of the alkyl ester monomers. The more preferred polymers are derived from 5 to 25 percent of the acid monomers and from 95 to 75 mole percent of the alkyl ester monomers with the alkyl groups in the latter containing from 6 to 18 carbon atoms. The most preferred polymers for the oil compositions are derived from 5–15 mole percent of the acid monomers and from 95 to 85 mole percent of alkyl ester monomers having 6 to 18 carbon atoms in the ester alkyl group.

The preferred polymers for the water-in-oil emulsion compositions are derived from 5 to 50 mole percent of the acid monomers and 95 to 50 mole percent of the alkyl ester monomers. The more preferred polymers are derived from 10 to 40 mole percent of the olefinically unsaturated carboxylic acid monomers and 90 to 60 mole percent of the alkyl ester monomers containing 6 to 18 carbon atoms in the ester alkyl groups. The most preferred polymers are derived from 15 to 30 mole percent of the acid monomers and 85 to 70 mole percent of the alkyl ester monomers containing 6 to 18 carbon atoms in the ester alkyl groups.

The preparation of the polymers from the olefinically unsaturated monomers is well documented in the literature and can be carried out by standard bulk, solution or emulsion techniques. Generally, the latter two are preferred with solution polymerization being most preferred. The polymerization of the monomers is catalyzed by free radical-generating catalysts such as peroxides, azo catalysts and the like. To be most effective, the reactor for such polymerizations should be purged with an inert gas in order to remove traces of oxygen. The solution polymerizations are run in a compatable solvent and the final polymer solution preferably contains 30 to 60 percent solids.

The molecular weight of the polymers used in the compositions may vary over a broad range. The molecular weight must be suitably large to provide the requisite binding effect. The upper limit is determined only by formulation requirements. As the molecular weight increases, the polymers tend to become too viscous to formulate easily into cosmetically-appealing compositions. Generally, polymers having a Brookfield viscosity between 50 and 100,000 cps, and preferably between 500 and 15,000 cps, when measured at 16.6 percent nonvolatiles will be useful in the compositions of the invention.

The acrylate polymers useful in the compositions are insoluble in water and must have a solubility parameter between about 6 and 10 in poorly hydrogen bonding solvents. The method for determining solubility parameter ranges of polymers and an extensive list of solvents (classified as either poorly hydrogen bonding, moderately hydrogen bonding, or strongly hydrogen bonding) are described in *Polymer Handbook* (edited by Bandrup and Immergut), pages IV-344–358. Acrylate polymers having the requisite solubility parameter will be soluble in the oil base of the compositions.

The compositions of the invention are of two basic types, i.e., oils and water-in-oil emulsions. The oil formulations are prepared by mixing the oil base, polymer and ultraviolet light absorbing material together and warming the mixture with slow agitation to about 140° F. The oil formulations generally contain about 0.5 to 20 percent by weight of the acrylate polymer, with the preferred range being from about 1.0 to 5.0 percent by weight. At levels below 0.5 percent, the polymer is less effective in holding a significant amount of the ultraviolet light-absorbing material on the skin when the skin is exposed to water. At levels above 20 percent, the formulation generally becomes sticky and unpleasant feeling.

The cosmetic oil base of the compositions may be solid or liquid, but the entire formulation should be somewhat fluid at skin temperatures for ease of application. Fragrances, fillers, dyes, colorants, preservatives, antioxidants and other such material conventionally used in sunscreening compositions may be included in minor amounts in the compositions without affecting the substantivity of the compositions.

When applied to human skin, these oil formulations form an oil film on the skin surface. This film gives the skin a moist, glossy appearance which many people find aesthetically pleasing. This film helps protect the skin from the drying effects of the environment, and the ultraviolet light-absorber protects the skin from the damaging rays of the sun. The polymer holds the ultraviolet light-absorber onto the skin so that a significantly greater percentage of erythema protection is provided after swimming or perspiring than with compositions without the polymer.

Compositions of the water-in-oil emulsion type generally contain between about 0.25 and 10 percent by weight of the acrylate polymer, with the preferred range being about 1 to 5 percent by weight. As indicated hereinabove, the preferred polymers for the emulsion-type formulations are those having emulsifying properties (i.e., those containing between 5 and 50 mole percent of acid monomers). Auxiliary emulsifiers may be employed to extend shelf life, but in general, the polymers alone are able to give emulsions with good stability. One particularly useful additive which has been employed is a copolymer of ethylene and acrylic acid (available commercially from Allied Chemical as AC-540 Polyethylene). This material acts as a good emulsion stabilizer, especially at higher temperatures.

The water-in-oil emulsions generally contain between 30 and 70 percent by weight of water. Although water is used in this system, the fact that the water evaporates is not an important feature of this invention. The film that is left behind on the skin in this system is an oil film identical to the film that is coated out from the oil system. A continuous, dry, polymeric film is not cast on the skin in either case.

Water-in-oil emulsions are generally prepared by heating the oil and water phases, and slowly adding the water phase to the oil phase with good agitation. Homogenization may be helpful, but it is not necessary. The addition of low levels of stabilizing ingredients in the water phase has been shown to be helpful. Salts such as magnesium sulfate have proven to be useful emulsion stabilizers, and they do not significantly affect the water resistance of the formulations. The addition of water soluble gums such as guar derivatives, xanthan gum, and aloe vera and thickeners such as hydroxy ethyl cellulose, hydroxy methyl cellulose and carboxy vinyl polymers have been found to be helpful in stabilizing the emulsions.

The sunscreening compositions of the invention may be further illustrated by the following nonlimiting examples. Ingredients used in the compositions are identified by commercial designation and manufacturer when they first appear. Unless otherwise indicated, the same commercial products are used throughout.

EXAMPLE 1

Water-in-oil Emulsion with Isooctyl Acrylate: Stearyl Methacrylate:Acrylic Acid Terpolymer (mole ratio 50:30:20)

A one quart amber bottle is charged with 360 parts isopropyl palmitate (IPP), ("Emerest" 2316, Malmstrom Chemicals, Emery Industries, Inc.), 106.25 parts isooctyl acrylate, 117.12 parts stearyl methacrylate, 16.63 parts acrylic acid and 2.40 parts 70 percent benzoyl peroxide ("Lucidol" 70, Lucidol Division, Penwalt Corporation). The system is degassed by pulling a vacuum and releasing the latter with nitrogen. The bottle is subsequently capped and placed in an Atlas Launderometer at 60°0 C. for 16 hours. The clear viscous polymer is allowed to cool. A diluted sample of the polymer (2 parts polymer mixture with 7 parts IPP) gave a Brookfield viscosity (Spindle #3, 30 rpm) of 5400 cps.

The terpolymer as diluted above was incorporated into a sunscreening composition of the water-in-oil emulsion type containing the following ingredients.

| Ingredient | Parts by Weight |
|---|---|
| Phase A | |
| Terpolymer solution | 9 |
| $C_{11}-C_{13}$ isoparaffinic solvent ("Isopar" L, Exxon Corp.) | 7 |
| $C_{12}-C_{15}$ alcohols ("Neodol" 25, Shell Chemical Co.) | 3 |
| Isopropyl palmitate | 5.9 |
| Polyethylene/acrylic acid copolymer (AC-540 Polyethylene, Allied Chemical Co.) | 2 |
| Paraffin wax (M.P. = 165° F.) ("Aristowax" 165, Witco Chemical Corp.) | 1 |
| Hydrogenated coconut oil ("Cobee" 92, M.P. 92° F., PVO International,Inc.) | 4 |
| Mineral oil/lanolin alcohol mixture ("Amerchol" L-101, Amerchol, Unit of CPC International, Inc.) | 1 |
| Octyl dimethyl PABA ("Escalol" 507 VanDyk and Co., Inc.) | 2.7 |
| Propyl paraben ("Lexgard" P, Inolex Corp.) | .15 |
| Phase B | |
| Deionized water | 63 |
| Xanthan gum ("Keltrol", Kelco Div., Merck & Co., Inc.) | .5 |
| Magnesium sulfate (USP, Mallinckrodt) | .15 |
| Methyl paraben ("Lexgard" M, Inolex Corp.) | .3 |
| Phase C | |
| Fragrance | .3 |
| | 100 |

The lotion is made by heating Phase A to 180° F. with slow agitation, and heating Phase B in a separate vessel to 180° F. with moderate agitation. Phase B is added to Phase A with rapid agitation, and the resulting creamy mixture is cooled with mixing to 100° F. The fragrance is then added. The composition is a smooth, white, creamy lotion which is barely pourable at room temperature. The lotion has a slightly oily feel.

The composition was tested for erythema protection on human volunteers using a 150 watt xenon arc solar simulator (available from Solar Light Company, Philadelphia, Pa. 19126). The composition (0.12 g) was applied to a 60 $cm^2$ area on the volar portion of the forearm, providing coverage of about 2.0 mg/$cm^2$. The amount of exposure necessary to elicit a minimal erythema response (minimum erythemal dose, MED) on the treated area was compared to the amount of exposure eliciting a MED on an untreated control area. This ratio is called the "protection factor." The protection factor for this composition was four, (i.e., the average person can withstand four times the amount of erythema radiation with the composition than without it.)

The protection factor can be changed by adjusting the level of ultraviolet light-absorber. The changes in the total weight can be compensated for by changing the level of isopropyl palmitate or combinations of the other oil phase ingredients. The protection factor data listed below shows the arithmetic means of protection factors determined on six human subjects for various levels of octyl dimethyl PABA. The standard deviation from the mean was approximately one for each of the data points.

| Wt.% octyl dimethyl PABA | Protection Factor |
|---|---|
| 2.0 | 3.71 |
| 2.5 | 4.25 |
| 2.7 | 4.55 |
| 3.0 | 4.83 |
| 3.5 | 7.58 |
| 3.7 | 8.25 |

Information from VanDyk & Co., Inc. on octyl dimethyl PABA indicates that a 1% solution by weight transmits about 13% of the incoming erythemal ultraviolet radiation. This would provide minimal protection, but could be beneficial to people who tan very well and rarely burn. The preferred range of octyl dimethyl PABA in the lotion is from 1 percent to 4 percent. This amount would provide protection factors from 2 to 8+. However, more or less could be used for those who desire extreme protection or for those who want very little protection.

EXAMPLE 2

Oil Formulation With Isooctyl Acrylate:Acrylic Acid Copolymer (Mole Ratio=90:10)

A three liter resin flask is charged with 1000 parts isopropyl palmitate (IPP), 958 parts isooctyl acrylate, 42 parts acrylic acid, and 7.14 g of 70 percent benzoyl peroxide at room temperature. The reactor is sealed, stirring initiated, and the system degassed by pulling a vacuum. The vacuum is broken with nitrogen and a nitrogen blanket is maintained over the system for the remainder of the polymerization. The reaction mixture is heated to 60° C. with heat lamps in 0.5 hrs., and the temperature is maintained at 60° C. (with an ice bath and later with heat lamps) for six hours. The resulting polymer is cooled to room temperature. A diluted sample of the water-white polymer (2 parts polymer mixture to 7 parts IPP) gave a Brookfield viscosity (Spindle 3, 30 rpm) of 1250 cps.

The copolymer as diluted above was incorporated into an oil-based composition containing the following ingredients:

| Ingredient | Parts by Weight |
|---|---|
| Copolymer solution | 9 |
| Carnation mineral oil (Saybolt Viscosity at 100° F. = 65/75, Witco Chemical Corp.) | 20 |
| Kaydol mineral oil (Saybolt Viscosity at 100° F. = 345/355, Witco Chemical Corp.) | 50 |
| Isopropyl palmitate | 8.55 |
| $C_{12}$-$C_{15}$ alcohols | 5 |
| Coconut oil (M.P. 76° F., "Cobee" 76, PVO International, Inc.) | 4 |
| Lanolin (Anhydrous USP grade, Robinson, Wagner Co., Inc.) | 1 |
| Octyl dimethyl PABA | 2 |
| Propyl paraben | .15 |
| Fragrance | .3 |
| | 100 |

The oil is made by warming all of the ingredients, except the fragrance, to 140° F. with slow agitation. The fragrance is added after the oil has cooled to about 100° F.

The composition is a smooth, clear, pale gold oil which is very easy to spread on the skin. The protection factor for this composition (determined as in Example 1) is three.

Four oils identical to that above except with 2 percent, 2.5 percent, 3 percent, and 3.5 percent octyl dimethyl PABA were prepared. Each of these oils was tested on six human volunteers to determine its protection factor using the solar simulator. The average protection factor ranged from 2.97 for the oil with 2 percent ultraviolet light absorber to 4.21 for the oil with 3.5 percent ultraviolet light absorber. An oil with 4 percent ultraviolet light absorber should meet the needs of most oil users who want considerable protection. It is not economically feasible to make a high screen oil due to the large amount of expensive ultraviolet absorber which would be required. Many oil users desire very minimal protection and oil compositions containing low levels of ultraviolet light absorber are generally acceptable.

The compositions described in Examples 1 and 2 are preferred formulations. The invention is by no means limited to the cosmetic oils shown in these compositions. Sunscreening compositions containing the polymers described herein can be formulated with vegetable oils, mineral oils, animal oils, saturated fatty acid esters, lanolin derivatives, or any mixture of oily materials which are toxicologically safe and well known in the cosmetic art. The choice of the oils depends upon the solubility characteristics of the polymer and the ultraviolet light absorber. The following examples illustrate other suitable compositions:

EXAMPLE 3

Following the procedure of Example 2, oil compositions were prepared with the following ingredients:

| Ingredient | Parts by Weight |
|---|---|
| Isooctyl acrylate homopolymer | 2 |
| Homomenthyl salicylate (Arsynco, Inc.) | 8 |
| Carnation mineral oil | 90 |
| | 100 |

EXAMPLE 4

| Ingredient | Parts by Weight |
| --- | --- |
| Isooctyl acrylate/acrylic acid (mole ratio = 90/10) | 2 |
| Homomenthyl salicylate | 8 |
| Isopropyl palmitate | 25 |
| Carnation mineral oil | 65 |
| | 100 |

EXAMPLE 5

| Ingredient | Parts by Weight |
| --- | --- |
| Isooctyl acrylate/acrylic acid (mole ratio = 60/40) | 2 |
| Octyl dimethyl PABA | 3 |
| Isostearyl alcohol ("Adol-66", Ashland Chemical Co.) | 15 |
| Isopropyl palmitate | 80 |
| | 100 |

Those skilled in the art would find little difficulty devising an oil phase which would be capable of dissolving both the polymer and the ultraviolet light absorber. For some polymers, mineral oil alone is adequate. This is the case with an isooctyl acrylate homopolymer. As the solubility parameter of the polymer increases, the solubility parameter of the oil solvents must also be increased. Accordingly, higher levels of more polar oils such as isopropyl palmitate, diisopropyl adipate, isostearyl alcohol, etc., should be used with compositions containing polymers of the type shown in Example 5.

Some ultraviolet light absorbers, such as 2-ethoxyethyl p-methoxycinnamate and ethyl dihydroxypropyl PABA are less soluble in mineral oil and can best be incorporated into an oily system through the addition of a solubilizing agent, such as PPG-15 stearyl ether ("Arlamol" E, ICI) or ethyoxylated lanolin derivatives ("Solulan", Amerchol). This is illustrated in the following Example:

EXAMPLE 6

| Ingredient | Parts by Weight |
| --- | --- |
| Isooctyl acrylate/acrylic acid (mole ratio = 90/10) | 2 |
| Ethyl dihydroxypropyl PABA ("Amerscreen" P, Amerchol, Unit of CPC International, Inc.) | 2 |
| PPG-20 lanolin ether ("Solulan" PB-20, Amerchol, Unit of CPC International, Inc.) | 20 |
| Isopropyl palmitate | 56 |
| Carnation mineral oil | 20 |
| | 100 |

EXAMPLE 7

The formulator has great freedom with the oil system of the invention since polymers are used that are very oil soluble. The use of large quantities of mineral oil in Example 2 was based largely on economic considerations. An example of an oil that has a unique feel on the skin is:

| Ingredient | Parts by Weight |
| --- | --- |
| Isooctyl acrylate/acrylic acid (mole ratio = 90/10) | 2 |
| Carnation mineral oil | 30 |
| Kaydol mineral oil | 11.5 |
| Isopropyl palmitate | 20 |
| Coconut oil | 15 |
| Diisopropyl adipate ("Ceraphyl" 230, VanDyk & Co., Inc.) | 8 |
| Peanut oil (Choice, Refined, Durkee Industrial Foods Group of SCM Corp.) | 5 |
| Palm oil (J-33, Durkee Industrial Foods Group of SCM Industries) | 5 |
| Octyl dimethyl PABA | 1.5 |
| Acetylated lanolin ("Modulan", Amerchol, Unit of CPC International, Inc.) | 1 |
| Cocoa butter (USP, "Olympus" Brand, Woodward & Dickerson, Inc.) | 1 |
| | 100 |

Any ultraviolet light absorber which has negligible water-solubility and good oil-solubility can be used in this system. As mentioned above, the oil phase constituents may be adjusted to account for the solubility characteristics of various ultraviolet light absorbers.

In Examples 8–10, water-in-oil type formulations were prepared using the method of Example 1. In Examples 11–13, oil formulations were prepared according to the method of Example 2.

EXAMPLE 8

| Ingredient | Parts by Weight |
| --- | --- |
| Homomenthyl salicylate | 7.93 |
| Acetylated lanolin | 1.22 |
| Isooctyl acrylate/octadecyl acrylate/acrylic acid terpolymer (mole ratio = 40/40/20) | 3.05 |
| $C_{11}$–$C_{13}$ isoparaffin solvent | 9.15 |
| Isopropyl palmitate | 9.15 |
| Isostearyl alcohol | 4.27 |
| Carnation mineral oil | 4.27 |
| Deionized water | 60.96 |
| | 100 |

When the heated water phase (180° F.) was added to the heated oil phase (180° F.) with stirring, a low viscosity, white, water-in-oil emulsion was formed which spread easily on the skin.

EXAMPLE 9

| Ingredient | Parts by Weight |
| --- | --- |
| Ethyl dihydroxypropyl PABA | 3.23 |
| Acetylated lanolin | 1.29 |
| $C_{11}$–$C_{13}$ isoparaffinic solvent | 10.98 |
| Isopropyl palmitate | 10.98 |
| Isostearyl alcohol | 5.81 |
| Isooctyl acrylate/acrylic acid copolymer (mole ratio = 70/30) | 3.10 |
| Deionized water | 64.61 |
| | 100 |

When made by the same method as Example 8, this formulation formed a smooth, white emulsion with a somewhat sticky feel.

EXAMPLE 10

The sunscreening agent used in this example is the bis-urea adduct of p-amino acetophenone and dimer diisocyanate

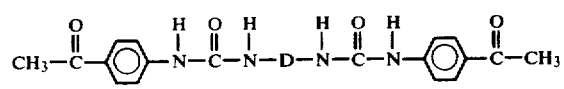

where D is a 36 carbon radical. This material and its method of preparation is described in U.S. Pat. No. 4,002,733.

| Ingredient | Parts by Weight |
| --- | --- |
| Sunscreening agent | 3.82 |
| Carnation mineral oil | 6.37 |
| $C_{12}$-$C_{14}$ isoparaffinic solvent | 12.74 |
| Isopropyl palmitate | 6.37 |
| Isostearyl alcohol | 6.37 |
| Isooctyl acrylate/acrylic acid (mole ratio = 94/6) | .64 |
| Deionized water | 63.69 |
| | 100 |

EXAMPLE 11

| Ingredient | Parts by Weight |
| --- | --- |
| Isooctyl acrylate/acrylic acid copolymer (mole ratio = 90/10) | 2 |
| Isopropyl palmitate | 23 |
| Carnation mineral oil | 50 |
| Kaydol mineral oil | 22 |
| Amyl dimethyl PABA ("Escalol" 506, VanDyk & Co., Inc.) | 3 |
| | 100 |

EXAMPLE 12

| Ingredient | Parts by Weight |
| --- | --- |
| Isooctyl acrylate/acrylic acid copolymer (mole ratio = 90/10) | 2 |
| Isopropyl palmitate | 48 |
| PPG-20 lanolin ether | 27 |
| Kaydol mineral oil | 20 |
| 2-ethoxyethyl p-methoxycinnamate (Giv-Tan F. Givaudan Corp.) | 3 |
| | 100 |

EXAMPLE 13

| Ingredient | Parts by Weight |
| --- | --- |
| Isooctyl acrylate/acrylic acid copolymer (mole ratio = 90/10) | 2 |
| Isopropyl myristate ("Emerest" 2314, Emery Industries, Inc.) | 90 |
| Isopropyl palmitate | 3 |
| 2-hydroxy-4-methoxy-benzophenone ("Uvinul" M-40, GAF Corp.) | 5 |

| Ingredient | Parts by Weight |
| --- | --- |
| | 100 |

EXAMPLE 14

Extraction Method for Substantivity

The substantivity of the compositions was determined by measuring the amount of ultraviolet light-absorber left on the skin after a vigorous water assault. The test was conducted in the following manner:

A master batch containing 4 percent by weight of the ultraviolet light-absorber octyl dimethyl PABA ("Escalol" 507, Van Dyk & Co.) and 96 weight percent of an oil solvent is prepared. The master batch is diluted with the acrylate polymer being evaluated in oil solvent to yield a test composition containing 3 percent by weight of the ultraviolet light-absorber, 2 percent by weight of the polymer, and 95 percent by weight of oil solvent.

A test site measuring 6×12 cm is marked on the volar portion of the forearm of a human subject. A barrier (Apiezon grease, Apiezon Products Ltd., Lond.) is applied around the test site to prevent spreading of the test composition. Eighty microliters of the test composition is applied and spread evenly over the test site. Five minutes later, the arm is exposed to a water assault by placing the arm in 5 gallons of circulating water at 35° C. in a 28×53×21 cm water bath with an initial water depth of 13.75 cm. The uppermost part of the arm is 1.25 cm below the water surface, and the center of the test site is 15.0 cm from the air nozzle. The hand is held at a 20°-30° angle from the horizontal. Agitation in the bath is obtained by pressurizing a 22.7×1.77 cm copper tube containing in a straight line, eleven holes, 1 mm in diameter and 2.05 cm apart, with an in-line air pressure of 2.13 kg per sq. cm. (30 lbs. per sq. in.). The air tube is placed 1.9 cm from the bath wall and 6.3 cm beneath the water surface with the holes positioned horizontally. With this arrangement, the air bubbles exit from the bath at approximately 7-9 cm from the nozzle and provide a very vigorous water flow over the test site. After 15 minutes, the arm is removed and air-dried using an air hose. Fifteen minutes later, two separate areas of the test site are extracted with 40 ml each of isopropyl alcohol in separate 4 oz. jars with a 3.86 cm diameter orifice. This is accomplished by placing the opened jar tightly against the arm in the test site with the palm of the test arm facing down. The arm and jar are moved to the horizontal position with respect to the jar, and the arm and jar are gently shaken back and forth 20 times to effect the extraction. The arm and jar are moved to the vertical position with respect to the latter and the jar removed and capped. On the test subject's other arm, a control formulation (without the polymeric binder) is evaluated in a similar way. The ultraviolet light absorbance at 310 nanometers of these solutions is read on a Beckman spectrophotometer from which the concentration of ultraviolet light-absorber can be calculated by reference to standardization curves with respect to the ultraviolet light-absorber.

The effectiveness of this method in extracting virtually 100 percent of the ultraviolet light-absorber present on the skin in the area circumscribed by the orifice of the jar was verified by initial tests. Therefore, all subsequent calculations were based on the theoretical amount of ultraviolet light-absorber applied to the test site.

The results of the test are summarized in the following table:

EVALUATION VIA THE EXTRACTIVE METHOD

| Composition Number | Polymer Mole Ratio | Monomer | Viscosity (cps)[2] | Solvent | UV absorbance × 1000 Polymer | Control[3] | Retention[1]-% Polymer | Control |
|---|---|---|---|---|---|---|---|---|
| 1. | 90:10 | IOA[4]:AA[5] | 684 | IPP[6] | 668 | 339 | 68 | 35 |
| 2. | 90:10 | IOA:AA | 1,400 | IPP | 718 | 336 | 74 | 37 |
| 3. | 90:10 | IOA:AA | 3,700 | IPP | 678 | 355 | 70 | 36 |
| 4. | 90:10 | IOA:AA | 12,000 | IPP | 897 | 310 | 92 | 32 |
| 5. | 80:20 | IOA:AA | 451 | IPP | 712 | 206 | 73 | 21 |
| 6. | 70:30 | IOA:AA | | IPP | 498 | 327 | 51 | 34 |
| 7. | 50:30:20 | IOA:SMA[7]:AA | 6,00 | IPP | 565 | 319 | 58 | 33 |
| 8. | 100 | BA[8] | 550 | IPP | 755 | 232 | 78 | 24 |
| 9. | 80:10 10 | IOA:BA:AA | 7,900 | IPP | 686 | 410 | 70 | 42 |
| 10. | 90:10 | IOA:AA[9] | 1,400 | IPP | 555 | 471 | 57 | 48 |
| 11. | 90:10 | IOA:AA[10] | 1,400 | IPP | 854 | 474 | 88 | 49 |
| 12. | 70:30 | IOA:AA | | DIPS[11] | 908 | 482 | 93 | 49 |
| 13. | 90:10 | IOA:MAA[12] | 578 | DIPS | 846 | 404 | 87 | 41 |
| 14. | 80:10:10 | IOA:BA:AA | 7,900 | DIPS | 994 | 632 | 102 | 65 |
| 15. | 40:40:20 | EHA[13]:MMA[14]:AA | 5,600 | DIPS | 764 | 262 | 78 | 27 |
| 16. | 90:10 | IOA:AA | 1,400 | DIPS | 866 | 429 | 89 | 44 |
| 17. | 60:20:20 | SMA:MM:AA | | DIPS | 670 | 212 | 69 | 22 |
| 18. | 100 | BA | 550 | DIPS | 743 | 532 | 76 | 54 |
| 19. | 100 | IOA | 260 | DIPS | 792 | 415 | 81 | 46 |
| 20. | 90:10 | IOA:AA | 1,400 | OA[15] | 842 | 753 | 86 | 77 |
| 21. | 90:10 | IOA:AA | 1,400 | ICA[16] | 891 | 582 | 92 | 60 |
| 22. | 90:10 | IOA:AA | 1,400 | DIPA[17] | 787 | 600 | 81 | 62 |
| 23. | Complete Oil Formation[18] of Example 2 | | | | 552 | 365 | 85 | 55 |
| Lotions[19] | | | | | | | | |
| 24. | 90:10 | IOA:MAA | 578 | IPP | 1,856 | — | 95 | — |
| 25. | 90:10 | SMA:AA | 48 | IPP | 1,732 | — | 89 | — |
| 26. | 35:45:20 | IOA:SMA:AA | 4,300 | IPP | 1,945 | — | 100 | — |
| 27. | 40:40:20 | EHA:MMA:AA | 5,600 | IPP | 1,606 | — | 82 | — |
| 28. | Complete Lotion Formulation of Example 1 | | | | 1,797 | — | 92 | — |

[1]Retention compared to absorbance of theoretical amount placed on test site (Theo. 975).
[2]Brookfield viscosity
[3]Solvent (oil) plus 3 weight percent octyl dimethyl PABA.
[4]Isooctyl acrylate.
[5]Acrylic Acid.
[6]Isopropyl palmitate.
[7]Stearyl methacrylate.
[8]Butyl Acrylate.
[9]0.5 weight percent polymer.
[10]10.0 weight percent polymer.
[11]Diisopropyl sebacate ("Unimate" DIPS, Union Camp).
[12]Methacrylic acid.
[13]Ethylhexyl acrylate.
[14]Methyl methacrylate.
[15]Oleyl alcohol ("Adol" 85, Ashland Chemical Co.).
[16]Iso-cetyl alcohol ("Standamul" G-16, Henkel, Inc.).
[17]Diisopropyl adipate.
[18]2% sunscreen agent-octyl dimethyl PABA
[19]Theoretical absorbance × 1000 = 1950.

EXAMPLE 15

The Extractive Method was also used to determine the effect of varying the ultraviolet light-absorber in the compositions. Results are summarized in the following table:

| Sunscreen Agent[1] | UV Absorbance[2] × 1000 Without Polymer Initial Final | | With Polymer Initial Final | | Retention-% Without Polymer | With Polymer |
|---|---|---|---|---|---|---|
| 1. Uvinul M-40[3] | 290 | 78 | 350 | 172 | 27 | 49 |
| 2. Homo-Menthyl Salicylate[4] | 123 | 60 | 130 | 107 | 49 | 82 |
| 3. Neo-Helipan E1000[5] | 913 | 436 | 861 | 519 | 48 | 60 |
| 4. Escalol 507[6] | 975[7] | 336 | 950 | 718 | 37 | 76 |

[1]3 weight percent sunscreen agent in IPP solvent. 2 weight percent 90:10 IOA:AA copolymer added where indicated.
[2]At 310 nm (nanometers)
[3]2-hydroxy-4-methoxybenzophenone (GAF Corp., Chem. Div.)
[4](Arsynco Inc.)
[5]Iso-amyl p-methoxycinnamate (Haarman & Reimer GmbH)
[6]Octyl p-dimethylaminobenzoate (Van Dyk & Co., Inc.)
[7]Theoretical amount which should be extracted The results show that the acrylate polymer significantly increases retention of all the ultraviolet light-absorbers on the skin.

EXAMPLE 16

Indoor Substantivity Test

The composition of Example 1 (Oil A) was tested against an identical composition without the acrylate polymer (Oil B) to determine whether the ability of the polymer to increase retention of the ultraviolet light-absorber on the skin during a water challenge correlated with increased erythema protection. The composition without the polymer is as follows:

| Oil B | Parts by Weight |
|---|---|
| Isopropyl palmitate | 17.55 |
| Carnation mineral oil | 20 |
| Kaydol mineral oil | 50 |
| $C_{12}$-$C_{15}$ alcohols | 5 |
| Coconut oil | 4 |
| Lanolin | 1 |
| Octyl dimethyl PABA | 2 |
| Propyl paraben | .15 |
| Fragrance | .3 |
| | 100 |

The test method is as follows:

Fair skinned, untanned human volunteers are used in the test. On the volar portion of each individual's forearm, a rectangular area approximately 240 cm² is marked off and 0.48 mililiters of the test composition is applied and rubbed in. Coverage is approximately 2 microliters/cm². After drying for 15 minutes, three circular spots on the treated area are exposed to ultraviolet light from a 150 watt Solar Simulator (Solar Light Co.) to elicit a burn with barely perceptible redness. The exposure times vary and depend upon the individual's specific skin type. Following these exposures, the forearm is immersed in an agitated water bath for 30 minutes using compressed air to agitate the water (as described in Example 14). Three different circular spots on the treated area are then exposed to ultraviolet light with each exposure slightly less than those prior to water immersion.

The procedure is repeated on the other forearm using compositions without the acrylate polymer, but containing the same concentration of ultraviolet light-absorber. Twenty-four hours following exposure to the ultraviolet light source, the burns are read by an observer with considerable experience reading such burns and scored using the following scale:

| | |
|---|---|
| 0 | - No burn |
| .1-.9 | - Faint burns which do not cover full circle |
| 1 | - Definite pink burn which covers full circle |
| 2 | - Bright red burn, with slight fuzziness around edges |
| 3 | - Severe burn, some swelling |
| 4 | - Very severe burn, blistering |

Before each composition was tested, the test subject's untreated resistance to burning was determined on each arm by administering four burns of varying duration. The burn times and readings are shown:

| Left Arm | | Right Arm | |
|---|---|---|---|
| Burn Time (min:sec) | Burn Reading | Burn Time (min:sec) | Burn Reading |
| 1:15 | .2 | 1:15 | 0 |
| 1:30 | .6 | 1:30 | .2 |
| 1:45 | .7 | 1:45 | .8 |
| 2:00 | 1 | 2:00 | 1 |

The results obtained with the test compositions are summarized below.

| Left arm - Oil B | | | |
|---|---|---|---|
| Before water assault | | After water assault | |
| Burn time | Burn rating | Burn time | Burn rating |
| 4:00 | .1 | 2:00 | 0 |
| 6:00 | .5 | 4:00 | .3 |
| 8:00 | 1 | 6:00 | 1.2 |
| Protection factor = 4 | | Protection factor <3 | |

| Right arm - Oil A | | | |
|---|---|---|---|
| Before water assault | | After water assault | |
| Burn time | Burn rating | Burn time | Burn rating |
| 4:00 | .1 | 2:00 | 0 |
| 6:00 | .3 | 4:00 | .2 |
| 8:00 | 1 | 6:00 | .5 |
| Protection factor = 4 | | Protection factor = 3.5 to 4 | |

Although both oils gave the same amount of protection before a water challenge, Oil A gave greater protection after a soak. This demonstrates that the addition of the polymer improves the water resistance of the ultraviolet light-absorber.

EXAMPLE 17

The test described in Example 16 was repeated using the following two compositions:

| Oil C | Oil D |
|---|---|
| 2% Butyl acrylate homopolymer | 3% Octyl dimethyl PABA |
| 3% Octyl dimethyl PABA | 97% Isopropyl palmitate |
| 95% Isopropyl palmitate | |
| 100% | 100% |

| Determination of untreated resistance to burning | | | |
|---|---|---|---|
| Left Arm | | Right Arm | |
| Burn time | Burn reading | Burn time | Burn reading |
| 1:15 | .1 | 1:15 | .7 |
| 1:30 | 1 | 1:30 | 1 |
| 1:45 | 1.4 | 1:45 | 1.4 |
| 2:00 | 1.5 | 2:00 | 1.6 |

Test Composition

| Left arm - Oil C | | | |
|---|---|---|---|
| Before water assault | | After water assault | |
| Burn Time | Burn rating | Burn time | Burn rating |
| 3:00 | .2 | 1:30 | .3 |
| 4:30 | 1 | 3:00 | .4 |
| 6:00 | 1.4 | 4:30 | 1 |
| Protection factor = 3 | | Protection factor = 3 | |

| Right arm - Oil D | | | |
|---|---|---|---|
| Before water assault | | After water assault | |
| Burn time | Burn rating | Burn time | Burn rating |
| 3:00 | .3 | 1:30 | .1 |
| 4:30 | .4 | 3:00 | .4 |
| 6:00 | 1 | 4:30 | 1 |
| Protection factor = 4 | | Protection factor = 3 | |

The protection provided by Oil D was decreased by the water challenge while the protection provided by Oil C was not. This indicates that the butyl acrylate homopolymer improves the water resistance of the ultraviolet absorber in this oil system.

EXAMPLE 18

This Example illustrates the effect of viscosity of the polymer on the feel of the oil formulation.

Six oils were formulated. These oils were identical except that a different isooctyl acrylate/acrylic acid copolymer was used in each. The basic oil formula was:

| Ingredient | Parts by Weight |
|---|---|
| Isooctyl acrylate/acrylic acid copolymer (mole ratio = 90/10) | 2 |
| Isopropyl palmitate | 10 |
| Carnation mineral oil | 45 |
| Kaydol mineral oil | 15 |
| Ethyl hexyl palmitate ("Ceraphyl" 368, Van Dyk & Co., Inc.) | 10 |
| Coconut oil | 10 |
| Cocoa butter | 1 |
| Acetylated lanolin | 1 |
| Octyl dimethyl PABA | 3 |
| Sesame oil (Refined, USP, Welch, Home & Clark Co., Inc. | 3 |
| | 100 |

Polymers used:
Viscosity (cps)*

| | | |
|---|---|---|
| Oil : E | 360 | (polymerized at 30% solids in IPP) |
| Oil : F | 515 | (polymerized at 35% solids in IPP) |
| Oil : G | 741 | (polymerized at 40% solids in IPP) |
| Oil : H | 992 | (polymerized at 45% solids in IPP) |
| Oil : I | 1000 | (polymerized at 50% solids in IPP) |
| Oil : J | 1780 | (polymerized at 55% solids in IPP) |

(Higher % solids when polymerized yield higher molecular weight polymers).

*Brookfield viscosity in isopropyl palmitate

All of the oils were clear, with no separation of the polymer. Oils E, F, and G were very light oils which had a "dry" feel and did not spread smoothly. They were also watery. Oil H was slightly watery, but spread much more smoothly than Oils E, F, or G. Oil I had an excellent, smooth feel on the skin. Oil J was very smooth, but it was rather greasy.

The polymer has a major effect on the feel of the oil. Polymers with low viscosities yield oils which have a dry feel. There is a range of viscosities which gives very pleasant feeling oils but when the viscosity is too high, the feel of the oil becomes greasy and sticky.

EXAMPLE 19

This Example illustrates the effect of viscosity on the substantivity of the oil compositions.

Five oils were formulated which were identical except that a different issoctyl acrylate/acrylic acid copolymer was used in each one. The basic oil formulations was as follows:

| Ingredient | Parts by Weight |
|---|---|
| Isooctyl acrylate/acrylic acid copolymer (mole ratio = 90/10) | 3 |
| Kaydol mineral oil | 20 |
| Carnation mineral oil | 45 |
| Isopropyl palmitate | 29 |
| Octyl dimethyl PABA | 3 |
| | 100 |

Polymers used:
Viscosity (cps)*

| | | |
|---|---|---|
| Oil : K | 12.7 | (polymerized at 18.9% solids) |
| Oil : L | 25.0 | (polymerized at 24.9% solids) |
| Oil : M | 48.0 | (polymerized at 28.9% solids) |
| Oil : N | 95.0 | (polymerized at 34.4% solids) |
| Oil : O | 228.0 | (polymerized at 39.3% solids) |

*Brookfield viscosity in ethyl acetate.

All five of these oils were clear with no polymer separation. The feel of Oils N and O was slightly smoother than the feel of the other oils.

Oils K, M, and O were tested for water resistance in the Indoor Substantivity Test as described in Example 16, except 0.155 g. of the composition was applied to a 36 cm² area of the forearm. A burn of six minutes (~3 MED) was administered to each square, and the subject than soaked his arm for 30 minutes in a bath of agitated water. Another six-minute burn was then administered to each area. The results were as follows:

| Oil | Burn Rating Before Soak | Burn Rating After Soak | Δ |
|---|---|---|---|
| K | 0 | 1 | 1 |
| M | .4 | 1.3 | .9 |
| O | .3 | .7 | .4 |

The water resistance of the ultraviolet light-absorber increases as the viscosity of the polymer increases.

EXAMPLE 20

Outdoor Substantivity Test

Resistance to removal of the compositions while swimming was determined by measuring the amount of sunburn protection remaining after swimming, compared to that provided without swimming.

Fair skin, untanned human volunteers were solicited for the sunburn test. A 144 cm² (12 cm × 12 cm) area was outlined on the upper center of each volunteer's back and this square subdivided into nine 16 cm² areas (4 cm × 4 cm). Through random selection, four of the nine squares were covered with four different test compositions, one test composition per square, (0.5 ml). The volunteers than swam for 30 minutes in an enclosed swimming pool keeping their back fully submerged. After swimming, the square on each volunteer's back was allowed to air dry, and then four of the five remaining untreated areas were covered with the same four different test compositions applied previously, one test composition per square. One square was left untreated to serve as a control site. Treating the squares in this manner permitted evaluation of the protection provided by each composition with and without a water challenge. Each volunteer laid in the prone position in the sun for 2 hours and 20 minutes. Untreated portions of the body were either covered with clothing or a complete sunscreen block was applied. Twenty-four hours after sun exposure, the squares on each volunteer's back were read for degree of redness by a physician who had no knowledge of the compositions being tested.

Burns were rated on the following scale:
0—no burn
1—minimal
2—mild
4—moderate—bright red
6—severe—some swelling
8—very severe—blistering Compositions of the invention (Lotion P and Oil Q), below were tested against commercially available sunscreening lotions and oils.

| (Water in Oil Emulsion) | |
|---|---|
| Lotion P Ingredient | Parts by Weight |
| Isooctyl acrylate/octadecyl acrylate/ acrylic acid (mole ratio - 45/35/20) | 2 |
| Acetylated lanolin | .5 |
| Cocoa butter | .5 |
| Isopropyl lanolate ("Amerlate" P, Amerchol, Unit of CPC International, Inc.) | 1 |
| C$_{11}$-C$_{13}$ isoparaffinic solvent | 7 |

19
-continued

(Water in Oil Emulsion)

| Isopropyl palmitate | 7 |
|---|---|
| Ethyl hexyl palmitate | 7 |
| Isostearyl alcohol | 4 |
| Hydrogenated coconut oil | 5 |
| Polyethylene/acrylic acid copolymer | 2 |
| Octyl dimethyl PABA | 3 |
| D.I. water | 60 |
| Xanthan gum | .5 |
| Magnesium sulfate | .2 |
| Fragrance | .3 |
| | 100 |

Oil Q

| Ingredient | Parts by Weight |
|---|---|
| Isooctyl acrylate/acrylic acid (mole ratio - 90/10) | 2 |
| Carnation mineral oil | 45 |
| Kaydol mineral oil | 15 |
| Isopropyl palmitate | 10 |
| Ethyl hexyl palmitate | 10 |
| Coconut oil | 10 |
| Cocoa butter | 1 |
| Acetylated lanolin | 1 |
| Sesame oil | 3 |
| Octyl dimethyl PABA | 3 |
| | 100 |

The following results were obtained:

| Test Composition | Burn Rating Before Swim | Burn Rating After Swim |
|---|---|---|
| Lotion P | 1 | 1 |
| Coppertone Lotion | 1 | 1 |
| Aztec Creamy Lotion | 1 | 3 |
| Sea & Ski Suntan Lotion | 2 | 3 |
| Untreated Control | — | 6 |
| Oil Q | 2 | 1 |
| Coppertone Oil | 1 | 3 |
| Sea & Ski Oil | 3 | 4 |
| Bain De Soleil Lotion (Oil) | 1 | 5 |
| Untreated Control | — | 4 |

This data demonstrates the superiority of the Oil Q over conventional oil formulations. The data also show that Lotion P and Coppertone are superior to the other emulsion type products tested.

What is claimed is:

1. A dermally-nonirritating sunscreening composition comprising:
   a nonvolatile, cosmetically-acceptable oil base;
   an effective amount of at least one ultraviolet light absorbing material which is substantially water-insoluble and soluble in said oil base; and
   at least 0.5 percent by weight based on the weight of said oil base of a water-insoluble acrylate polymer having a solubility parameter of 6 to 10 (cal./cc.)$^{1/2}$ in poorly hydrogen bonding solvents and a Brookfield viscosity between about 50 and 100,000 cps. when measured at 16.6 percent nonvolatiles.

2. The composition according to claim 1 wherein said polymer is derived from the polymerization of the same or different ester monomers of the formula:

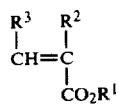

where $R^1$ is alkyl containing 1 to 18 carbon atoms, $R^2$ is hydrogen, methyl or —$CH_2CO_2H$, and $R^3$ is hydrogen, —$CO_2H$ or —$CO_2R^1$, provided that when $R^3$ is —$CO_2H$ or —$CO_2R^1$, $R^2$ is hydrogen; and optionally contains up to 50 mole percent of the same or different acid monomers of the formula:

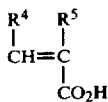

where $R^4$ is hydrogen or —$CO_2H$ and $R^5$ is hydrogen, methyl or —$CH_2CO_2H$, provided that when $R^4$ is —$CO_2H$, $R^5$ is hydrogen.

3. The composition according to claim 2 wherein said polymer contains from 100 to 70 mole percent of said ester monomers and from 0 to 30 mole percent of said acid monomers.

4. The composition according to claim 3 wherein said polymer contains from 95 to 85 mole percent of said ester monomers and from 5 to 15 percent of said acid monomers.

5. The composition according to claim 2 wherein said ester monomers are selected from the group consisting of alkyl esters of acrylic acid and methacrylic acid wherein the alkyl group contains 6 to 18 carbon atoms.

6. The composition according to claim 5 wherein said acid monomers are selected from the group consisting of acrylic acid and methacrylic acid.

7. The composition according to claim 2 further comprising between 30 and 70 percent by weight of water and wherein said polymer contains between 5 and 50 mole percent of said acid monomers.

8. The composition according to claim 7 wherein said polymer contains from 90 to 60 mole percent of said ester monomers and from 10 to 40 mole percent of said acid monomers.

9. The composition according to claim 8 wherein said ester monomers contain alkyl groups having 6 to 18 carbon atoms.

10. The composition according to claim 9 wherein said polymer comprises 85 to 70 mole percent of said ester monomers and from 15 to 30 mole percent of said acid monomers.

11. The composition according to claim 2 wherein said polymer has a Brookfield viscosity between 500 and 15,000 cps.

12. The composition according to claim 2 containing 0.5 to 20.0 percent by weight of said polymer based on the weight of said oil base.

13. The composition according to claim 5 wherein said ester monomers are selected from the group consisting of
   isooctyl acrylate
   stearyl methacrylate and
   octadecyl acrylate.

14. The composition according to claim 7 wherein said polymer contains 50 mole percent isooctyl acrylate, 30 mole percent stearyl methacrylate, and 20 mole percent acrylic acid.

15. The composition according to claim 6 wherein said polymer contains 90 mole percent isooctyl acrylate and 10 mole percent acrylic acid.

16. The composition according to claim 2 wherein said oil base comprises one or more oils selected from the group consisting of isopropyl palmitate mineral oil and isopropyl myristate.

17. A continuous oily film on human skin which provides erythema-protection from the ultraviolet radiation of the sun comprising:

a nonvolatile, cosmetically-acceptable oil base;

an effective amount of at least one ultraviolet light absorbing material which is substantially water-insoluble and soluble in said oil base;

at least 0.5 percent by weight of a water-insoluble polymer having a solubility parameter of 6 to 10 (cal./cc.)$^{1/2}$ in poorly hydrogen bonding solvents and a Brookfield viscosity between about 50 and 100,000 cps. when measured at 16.6 percent nonvolatiles, said polymer derived from the same or different ester monomers of the formula:

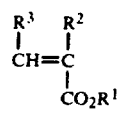

where $R^1$ is alkyl containing 1 to 18 carbon atoms, $R^2$ is hydrogen, methyl or —$CH_2CO_2H$ and $R^3$ is hydrogen, —$CO_2H$ or —$CO_2R^1$, provided that when $R^3$ is —$CO_2H$ or —$CO_2R^1$, $R^2$ is hydrogen, and optionally containing up to 50 mole percent of the same or different acid monomers of the formula:

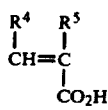

where $R^4$ is hydrogen or —$CO_2H$ and $R^5$ is hydrogen, methyl or —$CH_2CO_2H$, provided that when $R^4$ is —$CO_2H$, $R^5$ is hydrogen.

* * * * *